US00PP15799P2

(12) United States Plant Patent
Dümmen

(10) Patent No.: US PP15,799 P2
(45) Date of Patent: Jun. 14, 2005

(54) ***GERANIUM* PLANT NAMED 'DUEARTHEMIA'**

(50) Latin Name: *Pelargonium peltatum*
Varietal Denomination: Duearthemia

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 10/859,511

(22) Filed: Jun. 1, 2004

(51) Int. Cl.[7] ..... A01H 5/00
(52) U.S. Cl. ..... Plt./332
(58) Field of Search ..... Plt./332

(56) References Cited

PUBLICATIONS

UPOV–ROM GTITM Computer Database 2004/04, GTI Jouve Retrieval Software, Citation for 'Duearthemia'.*

* cited by examiner

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of Ivy *Geranium* plant named 'Duearthemia', characterized by its upright and outwardly spreading plant habit; freely basal branching habit; freely and early flowering habit; and dark red-colored double flowers.

1 Drawing Sheet

Botanical classification/cultivar denomination: *Pelargonium peltatum* cultivar Duearthemia.

BACKGROUND OF THE INVENTION

The present invention relates to a new and distinct cultivar of Ivy *Geranium* plant, botanically known as *Pelargonium peltatum,* and hereinafter referred to by the name 'Duearthemia'.

The new Ivy *Geranium* is a product of a planned breeding program conducted by the Inventor in Rheinberg, Germany. The objective of the breeding program was to develop new freely-flowering Ivy *Geraniums* with attractive flower and foliage colors.

The new Ivy *Geranium* originated from a cross-pollination made by the Inventor in May, 2000, of a proprietary selection of *Pelargonium peltatum* identified as code number F-02-01, not patented, as the female, or seed, parent with a proprietary selection of *Pelargonium peltatum* identified as code number F-09-14, not patented, as the male, or pollen, parent. The cultivar Duearthemia was discovered and selected by the Inventor as a flowering plant within the progeny from this cross in a controlled environment in Rheinberg, Germany in April, 2002.

Asexual reproduction of the new cultivar by terminal vegetative cuttings at Rheinberg, Germany since June, 2002 has shown that the unique features of this new Ivy *Geranium* are stable and reproduced true to type in successive generations of asexual reproduction.

SUMMARY OF THE INVENTION

The following traits have been repeatedly observed and are determined to be the unique characteristics of 'Duearthemia'. These characteristics in combination distinguish 'Duearthemia' as a new cultivar and distinguish it from other known Ivy *Geranium* cultivars:

1. Upright and outwardly spreading plant habit.
2. Freely basal branching habit.

3. Freely and early flowering habit.
4. Dark red-colored double flowers.

Compared to plants of the female parent selection, plants of the new Ivy *Geranium* are more compact and more freely flowering.

Compared to plants of the male parent selection, flowers of the new Ivy *Geranium* are more intense in color.

The new Ivy *Geranium* can be compared to plants of the cultivar Barock, not patented. In side-by-side comparisons conducted in Rheinberg, Germany, plants of the new Ivy *Geranium* differed from plants of the cultivar Barock in the following characteristics:

1. Plants of the new Ivy *Geranium* were shorter than plants of the cultivar Barock.
2. Leaves of the new Ivy *Geranium* were shorter than leaves of plants of the cultivar Barock.
3. Plants of the new Ivy *Geranium* were more freely flowering than plants of the cultivar Barock.
4. Flowers of plants of the new Ivy Geranium were more red in color than flowers of plants of the cultivar Barock.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Ivy *Geranium.*

The photograph comprises a side perspective view of typical flowering plants of 'Duearthemia' grown in a container.

DETAILED BOTANICAL DESCRIPTION

The cultivar Duearthemia has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the spring under commercial practice in a glass-covered greenhouse with day and night temperatures about 18° C., and light levels about 4,500 foot-candles. Plants were grown with three plants per container. Plants were pinched about three weeks after planting. Plants were about eight weeks from unrooted cuttings when the photograph and the detailed botanical description were taken.

In the following description, color references are made to The Royal Horticultural Society Colour Chart, 1995 edition, except where general terms of ordinary dictionary significance are used.

Botanical classification: *Pelargonium peltatum* cultivar Duearthemia.

Parentage:

*Female parent.*—Proprietary selection of *Pelargonium peltatum* identified as code number F-02-01, not patented.

*Male parent.*—Proprietary selection of *Pelargonium peltatum* identified as code number F-09-14, not patented.

Propagation:

*Type cutting.*—Terminal vegetative cuttings.

*Time to initiate roots.*—Summer: About 5 days at 20° C. Winter: About 7 days at 20° C.

*Time to develop roots.*—Summer: About three weeks at 20° C. Winter: About four weeks at 20° C.

*Root description.*—Fine; fibrous; white in color.

*Rooting habit.*—Freely branching.

Plant description:

*General appearance.*—Upright and outwardly spreading plant habit, rounded; densely foliated.

*Growth and branching habit.*—Moderately vigorous. Freely basal branching, about 13 lateral branches per plant.

*Plant height.*—About 24.5 cm.

*Plant width.*—About 12 cm.

*Lateral branches.*—Length: About 24 cm. Internode length: About 2.8 cm. Texture: Smooth. Color: 144A.

*Foliage description.*—Arrangement: Alternate, simple. Length: About 3.8 cm. Width: About 7.6 cm. Shape: Reniform. Apex: Acute. Base: Peltate. Margin: Crenate. Venation pattern: Palmate. Texture, upper and lower surfaces: Smooth. Color: Developing foliage, upper surface: 137A. Developing foliage, lower surface: 137C. Fully expanded foliage, upper surface: 137A; no distinct zonation pattern. Venation, upper surface: 144A. Venation, lower surface: 144B. Petiole: Length: About 4.8 cm. Diameter: About 1.8 mm. Color, upper and lower surfaces: 144A.

Flower description:

*Flower arrangement.*—Dark red-colored double flowers arranged in rounded hemispherical umbels arising from apical leaf axils. Umbels displayed above the foliage on upright peduncles. Flowers rounded in form. Umbels persistent, flowers not persistent. Flowers not fragrant.

*Quantity of flowers.*—Freely flowering; at full flower, plants have about eight open umbels with about nine flowers per umbel.

*Flowering season.*—Flowering continuous spring through summer.

*Flower longevity.*—Flowers last about five to seven days on the plant.

*Umbel size.*—Diameter: About 6.9 cm. Height: About 4.7 cm.

*Flower size.*—Diameter: About 4.2 cm. Depth (height): About 1.9 cm.

*Flower buds.*—Length: About 1.1 cm. Diameter: About 6 mm. Shape: Ovoid. Color: 144A.

*Petals.*—Quantity per flower: About six or seven. Length: About 2.4 cm. Width: About 1.5 cm. Shape: Obovate. Apex: Rounded. Base: Attenuate. Margin: Sinuate. Texture, upper and lower surfaces: Smooth. Color: When opening and fully developed, upper surface: 45B; towards base, 53A; color does not fade with development. When opening and fully opened, lower surface: 53C to 53D; towards base, 61A to 61B. Venation, upper surface: 45B. Venation, lower surface: 53C to 53D.

*Petaloids.*—Quantity per flower: About twelve. Length: About 2 cm. Width: About 1.2 cm. Shape: Obovate. Apex: Rounded. Base: Attenuate. Margin: Sinuate. Texture, upper and lower surfaces: Smooth. Color: When opening and fully developed, upper surface: 45B; towards base, 53A; color does not fade with development. When opening and fully opened, lower surface: 53C to 53D; towards base, 61A to 61B. Venation, upper surface: 45B. Venation, lower surface: 53C to 53D.

*Sepals.*—Quantity per flower: About five to six, arranged in a single whorl. Length: About 1.3 cm. Width: About 4 mm. Shape: Elongated, tapering. Apex: Apiculate. Margin: Entire. Texture, upper and lower surfaces: Smooth. Color, upper and lower surfaces: 144A.

*Peduncle* (*umbel stem*).—Length: About 6.5 cm. Diameter: About 2 cm. Angle: Erect. Strength: Moderately strong. Texture: Smooth. Color: 144A.

*Pedicel* (*individual flower stem*).—Length: About 2 cm. Diameter: About 2 mm. Angle: Erect. Strength: Moderately strong. Texture: Pubescent. Color: 144A.

*Reproductive organs.*—Androecium: Anther quantity per flower: About six to seven. Anther length: About 3 mm. Anther shape: Ovate. Anther color: 79A. Pollen amount: Moderate. Pollen color: 28A. Gynoecium: Pistil quantity per flower: One. Pistil length: About 1.1 cm. Stigma shape: Five-parted, star-shaped. Stigma color: 59A. Style length: About 4.7 mm. Style color: 2D. Ovary color: 144A.

*Seed/fruit.*—Development of seeds and fruit have not been observed.

Disease/pest resistance: Plants of the new Ivy *Geranium* have not been observed to be resistant to pathogens and pests common to Ivy *Geranium.*

It is claimed:

1. A new and distinct cultivar of Ivy *Geranium* plant named 'Duearthemia', as herein illustrated and described.

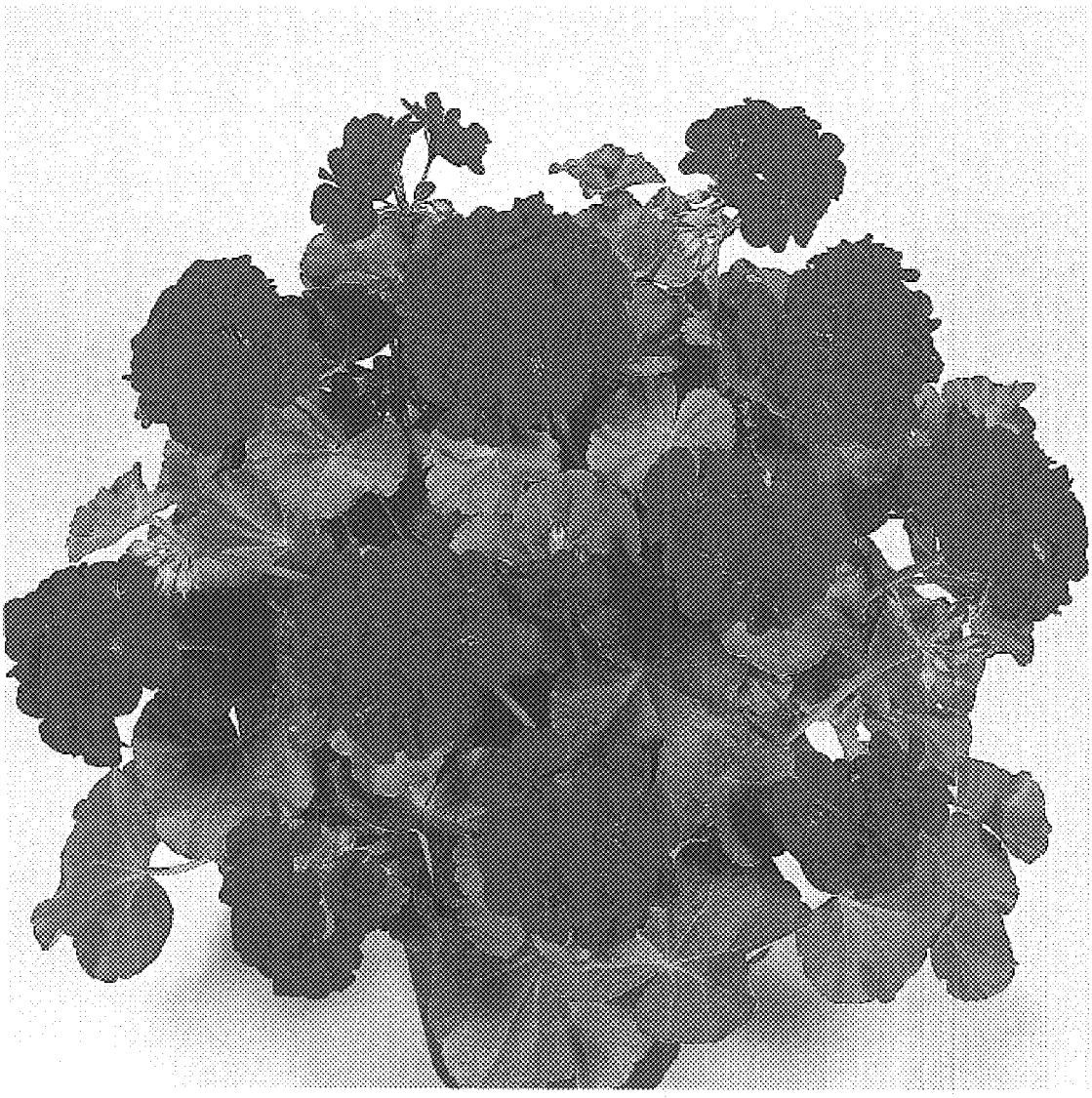

* * * * *